United States Patent [19]
Zafred

[11] Patent Number: 4,752,127
[45] Date of Patent: Jun. 21, 1988

[54] OPTICAL TUBE INSPECTION APPARATUS

[75] Inventor: Paolo R. Zafred, Pittsburgh, Pa.

[73] Assignee: Westinghouse Electric Corp., Pittsburgh, Pa.

[21] Appl. No.: 711,421

[22] Filed: Mar. 13, 1985

[51] Int. Cl.[4] .................... G02B 23/26; G01N 21/88
[52] U.S. Cl. .................................. 356/241; 250/341
[58] Field of Search ................ 356/241; 250/341, 350, 250/351

[56] References Cited

U.S. PATENT DOCUMENTS

| | | | |
|---|---|---|---|
| 2,682,800 | 7/1954 | Ennis et al. | |
| 2,735,017 | 2/1956 | Beard et al. | |
| 2,899,856 | 8/1959 | Shull | 356/241 |
| 2,987,960 | 7/1961 | Sheldon | |
| 3,637,314 | 1/1972 | Groot | 356/241 |
| 3,954,136 | 5/1976 | Gugel | 165/11 A |
| 4,021,840 | 5/1977 | Ellsworth et al. | 358/101 |
| 4,172,492 | 10/1979 | Abell et al. | 165/11 A |
| 4,199,258 | 4/1980 | Dau | 356/241 |
| 4,216,893 | 8/1980 | Glatthorn | 228/45 |
| 4,231,419 | 11/1980 | Gugel | 165/11 A |
| 4,249,413 | 2/1981 | Denis | 165/11 A |
| 4,255,762 | 3/1981 | Takeyasu et al. | 358/100 |
| 4,298,054 | 11/1981 | Adamowski | 165/11 A |
| 4,317,632 | 3/1982 | Orphan et al. | 356/241 |
| 4,383,761 | 5/1983 | Jones | 356/241 |
| 4,493,554 | 1/1985 | Pryor et al. | 356/241 |

FOREIGN PATENT DOCUMENTS

| | | |
|---|---|---|
| 2519761 | 7/1983 | France |
| 2068114 | 1/1980 | United Kingdom |
| 386366 | 9/1973 | U.S.S.R. |

OTHER PUBLICATIONS

"Photoelectric controls & Reference Manual", Banner Engineering Corp., 1983, pp. Cover, 40, 47, 57-61, 63, 65, 66, 77, 85, 95, 98, 99, 101, 104, 112, 117, 118, 121, 125, 127, 129, 130, 131, 133, 135, 145, 146, 147, 163, 164, 165 and 179.
Brochure entitled "'M' Series Modulated LED Amplifiers", pp. 61 and 77.
MetroByte Corporation brochure entitled "16 Channel High Speed A/D Interface with DMA Model Dash-16".
C.E.G.B. Technical Disclosure Bulletin, No. 253, Sep. 1975.

Primary Examiner—Vincent P. McGraw

[57] ABSTRACT

A tube inspection apparatus includes a probe which carries along the tube one or more infrared emitters and a plurality of infrared detectors. In one embodiment there is one emitter and in another embodiment the number of emitters equals the number of detectors. A cylindrical sleeve encircles a portion of the probe and has resilient fingers slidably frictionally engageable with the inner surface of the tube for centering the probe, equiangularly spaced-apart slots being formed in the sleeve to accommodate light transmission therethrough. Fiber optic bundles in the probe have their inner ends optically coupled to the emitters and detectors, with the outer ends being respectively disposed in alignment with the openings. A cam adjusting means is axially movable on a threaded rod for radially moving the outer ends of the fiber bundles to adjust their spacing from the inner surface of the tube. Preferably, each emitter is modulated for eliminating the effects of ambient light.

16 Claims, 3 Drawing Sheets

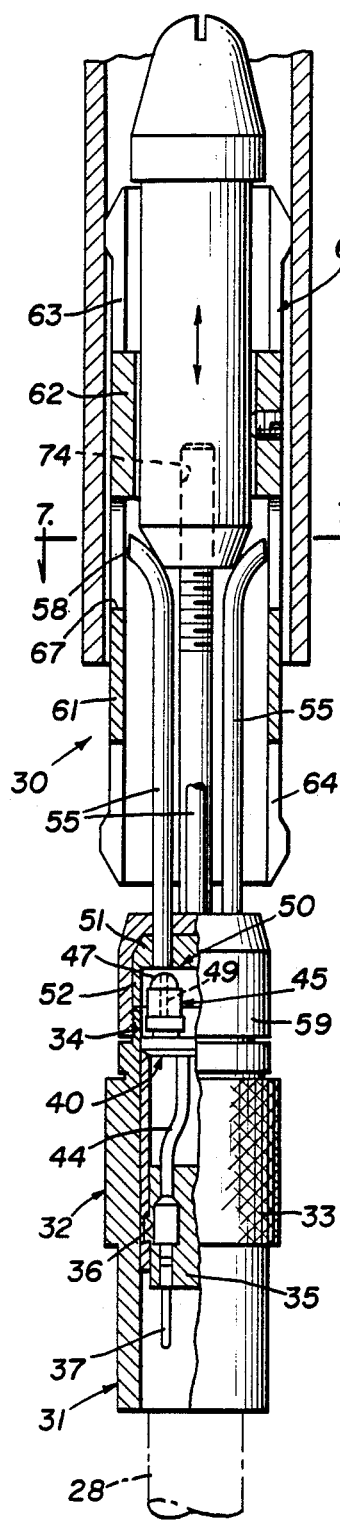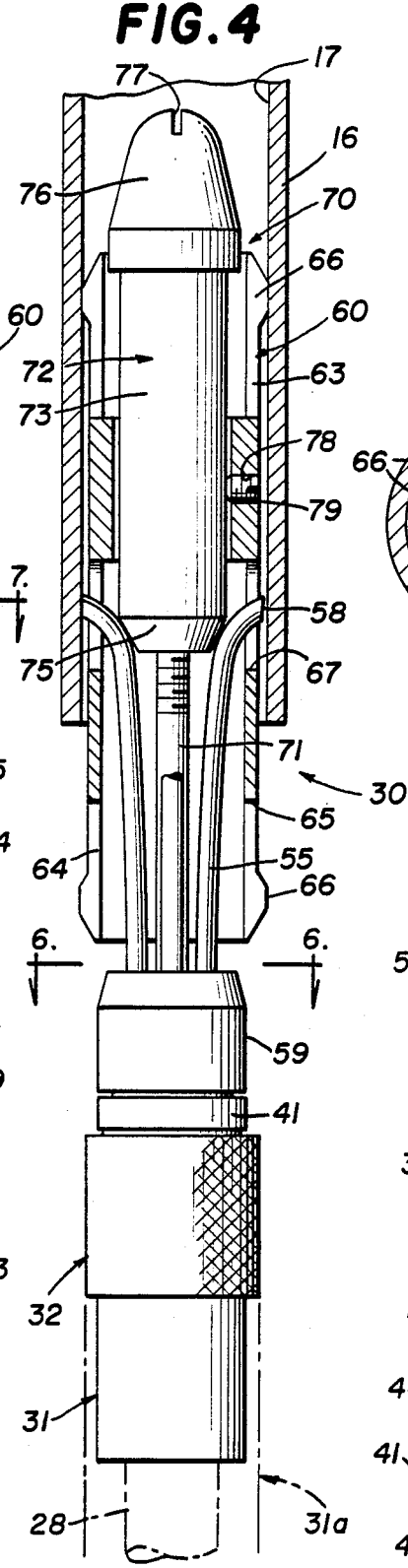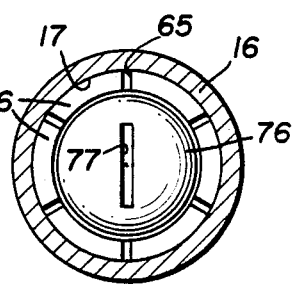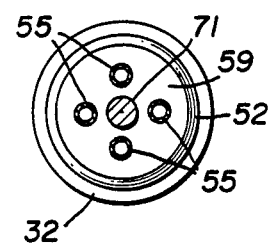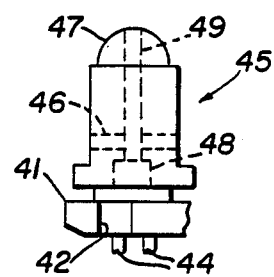

OPTICAL TUBE INSPECTION APPARATUS

BACKGROUND OF THE INVENTION

1. Field of the Invention:

The present invention relates to apparatus for the remote inspection of the interior surfaces of tubes. The invention has particular application to the maintenance of steam generators, particularly nuclear power plant steam generators.

2. Descritpion of the Prior Art:

A nuclear steam generator contains many vertical tubes arranged in close relationship to each other. A primary fluid, having been heated by circulation though the nuclear reactor core, is circulated through the tubes. At the same time, a secondary fluid, or feedwater, is circulated around the tubes in heat transfer relationship therewith, thereby transferring heat from the primary fluid in the tubes to the secondary fluid surrounding the tubes, causing a portion of the secondary fluid to be converted to steam.

Isolation of the radioactive primary fluid from the secondary fluid in a nuclear steam generator is critical. Accordingly, the integrity of the heat exchanger tubes is also critical, and test and maintenance procedures have been developed for inspection of the tubes and the correction of defects therein. One technique for correcting local defects in the tubes is sleeving, i.e., mounting an auxiliary tube section inside the defective tube to span the defective region, thereby returning the tube to its normal heat transfer capacity.

Fundamental to both the inspection and maintenance procedures is the insertion of probe devices into the tubes for detecting defective regions and for inspecting the repairs. One such inspection is conducted during the sleeving operation. The sleeves are brazed or welded to the interior surfaces of the tubes, and these surfaces, which typically have an accumulation of oxidation, must be honed (or wire brushed) in preparation for brazing or welding. After the honing, the surface must be inspected to be sure that it is in proper condition for brazing, and this necessitates that the inspection probe be able to distinguish between the bright or shiny honed surface and the surrounding dull or oxidized surface of the tube.

Optical inspection techniques have been used for directly viewing or scanning the interior surface of the tube, as with fiber optic probes. Such probes may involve transmitting light into the tube from a remote light source through a long fiber optic cable, the reflected light being returned through another portion of the cable to a camera or other viewing means at the remote location. But detection capability may be restricted with such systems due to the optical losses in the long fiber optic cables or as a result of inspecting light-absorbent or dark surfaces, such as those coated with oxide deposits, which require higher levels of illumination. Furthermore, such fiberscopes are very expensive, require delicate handling, are subject to easy breakage, and must be rotatable to obtain complete circumferential coverage of a tube. Also, such optical imaging systems rely on the subjective determination of the individual inspector, who bases his determination solely on what he sees. Thus, the results are dependent on the competence and visual acuity of the operator, making standardization difficult, if not impossible. Furthermore, the measurements from such optical imaging systems are degraded by the effects of ambient light.

It is known to minimize the problem of optical losses by mounting the light source and the light detection means on the probe, so that only electrical signals are transmited over the long cable which extends to the remote control location. But such systems are still subject to the other disadvantages of optical imaging systems, discussed above.

While the present invention relates principally to the inspection of the interior surfaces of tubes in preparation for sleeving, it also would have more general application for in-service inspection of steam generator tubing, e.g., for defect detection, when a quick diagnosis of tube condition is required.

Various inspection techniques have been used heretofore for such purposes, including ultrasonic and eddy current techniques. Ultrasonic techniques have the disadvantage that the ultrasonic energy must be mechanically coupled into the tube wall, as by a liquid coupling medium. Eddy current techniques are only usable with certain materials, and the measurements are affected by the presence of structures, such as support plates, external to the tube. Furthermore, such prior techniques have typically entailed subjective operator interpretation of data, such as comparison of the data with standard profiles, and this leads to inaccuracies and inconsistencies in the results, since it is dependent upon individual operator skill.

SUMMARY OF THE INVENTION

It is a general object of the present invention to provide inspection apparatus for inspecting the interior surfaces of tubes, which apparatus avoids the disadvantages of prior devices, while affording additional structural and operating advantages.

An important object of the invention is the provision of an optical inspection apparatus, which provides for accurate and unambiguous measurements of the condition of the interior surface of the tube.

It is another object of the invention to provide an inspection apparatus of the type set forth, which affords substantially complete circumferential coverage without rotation of the device.

Still another object of the invention is the provision of an inspection apparatus of the type set forth which is substantially immune to the effects of ambient light.

In connection with the foregoing object, another object of the invention is the provision of an optical inspection system of the type set forth, which provides for unambiguous discrimination among a number of emitter/detector units.

Still another object of the invention is the provision of an optical inspection apparatus of the type set forth which provides for simple adjustment of the calibration of the apparatus.

Yet another object of the invention is the provision of an optical inspection apparatus of the type set forth, which is of rugged, yet simple and economical construction, affording easily removable and replaceable modular components.

These and other objects of the invention are attained by providing apparatus for inspecting the interior surface of a tube, comprising: light source means, a plurality of light sensing means for receiving light from circumferentially spaced portions of the interior surface and generating electrical signals in response thereto, and probe means for supporting the light source means and the light sensing means and moving them along the inside of the tube.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there are illustrated in the accompanying drawings preferred embodiments thereof, from an inspection of which, when considered in connection with the following description, the invention, its construction and operation, and many of its advantages should be readily understood and appreciated.

FIG. 3 is a further enlarged view in vertical section taken along the line 3—3 in FIG. 2, and illustrating the fiberoptic sensors in their fully retracted positions;

FIG. 4 is a view similar to FIG. 3, and illustrating adjustment of the fiberoptic sensors to their radially extended positions;

FIG. 5 is a top plan view of the probe assembly of FIG. 4;

FIG. 6 is a view in horizontal section taken along the line 6—6 in FIG. 4;

FIG. 9 is a further enlarged, fragmentary, side elevational view of one of the emitter/detector units of the probe of FIGS. 2 and 3;

DESCRIPTION OF THE PREFERRED EMBODIMENTS

Figure 1:
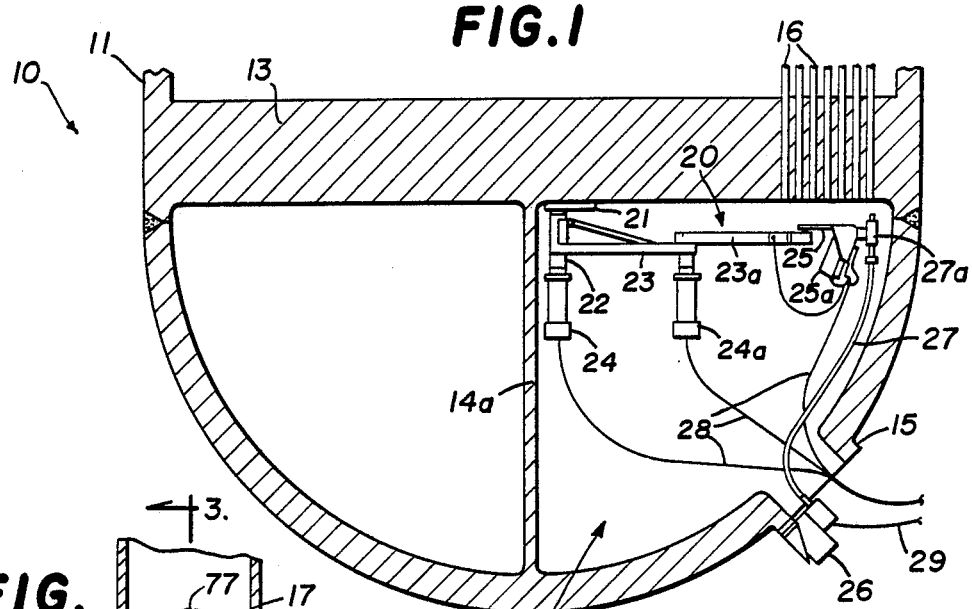
FIG. 1 is a fragmentary view in vertical section of the lower end of a nuclear steam generator vessel, illustrating the use of an optical inspection system constructed in accordance with and embodying the features of the present invention.

Referring to FIG. 1, there is illustrated a nuclear steam generator vessel, generally designated by the numeral 10, which includes a cylindrical side wall 11 and a partspherical bottom wall 12. The lower end of the side wall 11 is closed by a circular tube sheet 13, which cooperates with the bottom wall 12 to define therebetween two channel head chambers 14 separated by a separator plate 14a. Communicating with each of the chambers 14 is a manway 15 and a nozzle (not shown). The nozzles are adapted to be coupled by suitable conduits to an associated nuclear reactor for circulating primary coolant between the nuclear reactor and the steam generator vessel 10. More specifically, the primary coolant enters one of the chambers 14 and then flows upwardly through a plurality of inverted U-shaped heat exchanger tubes 16 (only a few of which are shown), the lower ends of which are received in complementary openings in the tube sheet 13, with each tube 16 having the two lower ends thereof respectively communicating with the two chambers 14. Each of the tubes 16 has a circularly cylindrical inner surface 17 (see FIG. 2). The primary coolant circulates from one chamber 14 through the tubes 16 to the other chamber 14 and thence back to the nuclear reactor. A secondary coolant surrounds the tubes 16 above the tube sheet 13 in heat exchange relationship therewith, the secondary coolant being converted to steam in a known manner.

The present invention relates to a probe assembly 30 for insertion into a tube 16 for inspection thereof. For this purpose there may be utilized a standard eddy current probe insertion assembly 20, of the type disclosed in U.S. Pat. No. 4,302,146, a base plate 21 secured to the underside of the tube sheet 13 and carrying a depending post 22. Extending radially from the post 22 in cantilever fashion for pivotal movement with respect to the axis thereof is an elongated arm 23 to which is pivotally mounted an extension arm 23a, the pivotal movement of the arms 23 and 23a being respectively controlled by drive units 24 and 24a. A camera arm assembly 25 is mounted on the distal end of the extension arm 23a and is longitudinally reciprocatively and pivotally movable with respect thereto, the camera arm assembly 25 including a video camera 25a. Mounted on the manway 15 is a probe pusher 26 for pushing a probe through a guide sleeve 27 and an insertion nozzle 27a, carried by the end of the camera arm assembly 25, for inserting an associated probe into a selected one of the tubes 16. The drive units 24 and 24a and the camera 25a are coupled to control cables 28, and the probe pusher 26 is coupled to a control and data transmission cable 29, the cables 28 and 29 extending to a remote control station.

Figure 2:
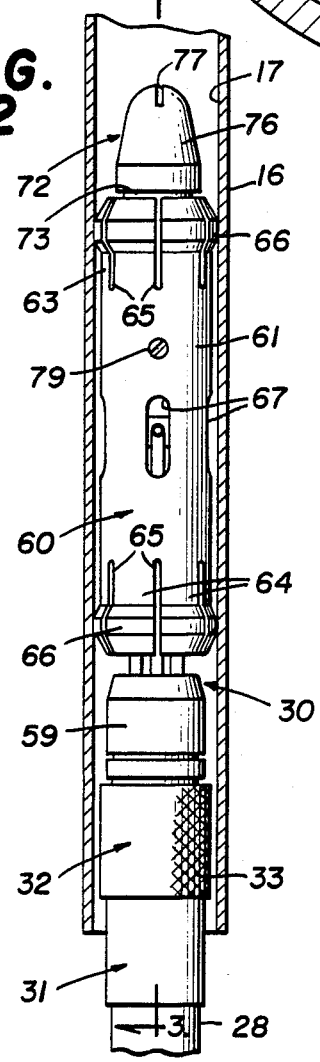
FIG. 2 is an enlarged fragmentary view in partial section of an inspection probe in accordance with a first embodiment of the present invention, shown in position in one of the heat exchanger tubes of the steam generator vessel of FIG. 1.

Referring now to FIGS. 2–4, the probe assembly 30 includes a male plug connector 31, adapted for coupling to an associated female receptacle 31a (see FIG. 4) to which is connected one end of the associated control and data transmission cable 29. The plug connector 31 includes a cylindrical coupling sleeve 32 having an externally knurled portion 33 intermediate the ends thereof and an externally threaded portion 34 at the upper end thereof. A cylindrical insert 35 is receivable telescopically within the coupling sleeve 32, the insert 35 being substantially cylindrical and having a radially outwardly extending annular flange 36 intermediate the ends thereof. The insert 35 carries a plurality of pins 37 adapted for coupling to corresponding female contacts of the receptacle 31a. Disposed telescopically within the coupling sleeve 32 and in surrounding relationship with the insert 35 is a split sleeve 38 having an associated recess for receiving the flange 36, for positioning the insert 35 within the coupling sleeve 32.

The upper end of the split sleeve 38 is disposed adjacent to the lower end of the externally threaded portion 34 and receives thereon a transducer assembly, generally designated by the numeral 40. More specifically, referring also to FIG. 9, the transducer assembly 40 includes a circular base 41 which rests on the upper end of the split sleeve 38 and has shallow notches or slots 42 formed in the outer edge thereof. Mounted on the base 41 are a plurality of emitter/detector units 45 (one shown). Three or four of the units 45 may be provided, four being provided in the illustrated embodiment.

Each of the emitter/detector units 45 is a commercially available chip unit, such as one of the S-27 Series manufactured by Skan-A-Matic, including an infrared light emitting diode ("LED") 46 and an associated epoxy lens 47. A fiberoptic rod 49 extends axially through the center of the lens 47 and communicates with a phototransistor 48 in the base of the emitter/detector unit 45. The leads of the LED 46 and the phototransistor 48 are respectively connected to pairs of wires 44, which are in turn connected to the pins 37 of the insert 35.

Figure 8:
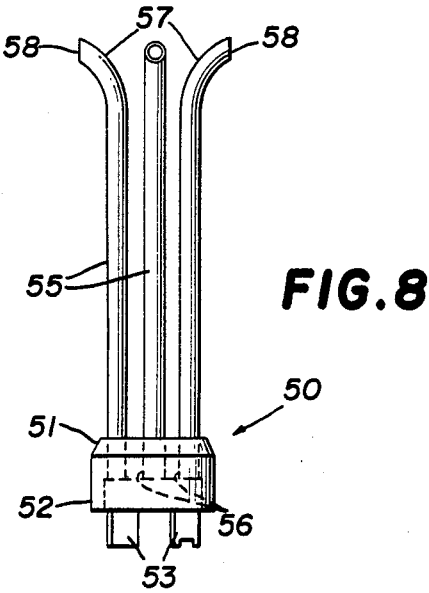
FIG. 8 is a fragmentary side elevational view of the sensor assembly of the probe of FIGS. 3 and 4.

Each of emitter/detector units 45 projects upwardly a slight distance above the upper end of the coupling sleeve 32. Referring also to FIGS. 6 and 8, overlying the transducer assembly 40 is a sensor unit 50 which includes a circular base 51 having a depending cylindrical wall 52 integral therewith. The lower end of the cylindrical wall 52 rests upon the upper end of the coupling sleeve 32, and is provided with one or more depending anti-rotation keys 53 (see FIG. 8) adapted for keying engagement in the slots 42 of the transducer assembly base 41. Carried by the sensor unit 50 are four fiberoptic bundles 55, each having an inner end 56 which extends through the base 51 and overlies an associated one of the emitter/detector units 45 coaxially therewith, so that the outer fibers of the bundle 55 are optically coupled to the LED 46 and the central fibers of the bundle 55 are optically coupled to the fiberoptic rod 49 of the phototransistor 48. Each of the fiber bundles 55 is elongated and has a outwardly curved upper end 57 which terminates in an outer end surface 58 which defines an optical interface. A coupling nut 59 is seated down over the base 51 of the sensor unit 50 and is threadedly engaged with the externally threaded portion 34 of the plug connector 31, securely to hold the plug connector 31, the transducer assembly 40 and the sensor unit 50 in an assembled condition.

Figure 7:
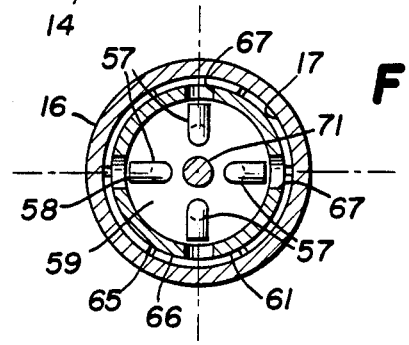
FIG. 7 is a view in horizontal section taken along the line 7—7 in FIG. 3.

Referring also to FIG. 7, the probe assembly 30 also includes an elongated centering sleeve 60, having a tubular body 61 with a thickened wall portion 62 intermediate the ends thereof, the inner diameter of which thickened portion 62 is smaller than the inner diameter of the remainder of the tubular body 61. The tubular body 61 is bifurcated at the upper and lower ends thereof to define a plurality of upper fingers 63 and a plurality of lower fingers 64, each of the fingers 63 and 64 being separated from adjacent fingers by notches 65. Formed in the outer surface of each of the fingers 63 and 64 is an enlarged-diameter bearing bead 66, the beads 66 being circumferentially aligned and cooperating to define an enlarged-diameter portions which have an outer diameter slightly greater than the diameter of the interior surface 17 of an associated one of the tubes 16. The fingers 63 and 64 are radially flexible to permit insertion of the centering sleeve 60 into an associated one of the tubes 16, accommodate frictional sliding movement thereof along the interior surface 17 of the tube 16, and minimize wobbling as the probe assembly 30 is moved along the tube 16. The tubular body 61 is provided immediately below the thickened portion 62 with a plurality of equiangularly spaced-apart slots 67, the slots 67 preferably being equal in number to and disposed respectively for alignment with the outer end surfaces 58 of the fiber bundles 55.

There is also provided an adjustment assembly 70, including an elongated cylindrical threaded rod 71 disposed coaxially with the centering sleeve 60. The lower end of the threaded rod 71 is fixedly secured to the base 51 of the sensor unit 50, and the upper end of the rod 71 is threadedly engaged with the lower end of a cam member 72. More specifically, the cam member 72 includes an elongated cylindrical body 73 having an internally threaded axial bore 74 at the lower end thereof in which the threaded rod 71 is received. The cam member 72 is also provided with a frustoconical cam surface 75 at its lower end and is provided with an enlarged-diameter head 76 at the upper end thereof. Formed axially in the enlarged head 76 is a diametrical slot 77 for receiving an associated tool, such as a screwdriver, for fine adjustment. The thickened portion 62 of the centering sleeve 60 has one or more radial bores 78 formed therein (see FIGS. 3 and 4) in which are respectively received set screws 79 for fixedly securing the centering sleeve 60 to the cam member 72.

It will be appreciated that when the probe assembly 30 is inserted into an associated tube 16, the fiber bundles 55 respectively view equal circumferentially spaced sectors of the interior surface 17 of the tube, the fiber bundles 55 respectively viewing through the slots 67 in the centering sleeve 60. In this regard, it is important that the radial distance between the interface-defining outer end surfaces 58 of the fiber bundles 55 and the interior surface 17 of the tubes 16 be accurately set to achieve maximum current output from the emitter/detector units 45. It is a significant feature from the present invention that the adjustment assembly 70 permits ready adjustment of this distance.

More specifically, the cam member 72 is rotated by the use of a screwdriver, or the like, inserted in the slot 77, thereby moving the cam 72 axially along the threaded rod 71. The cam surface 75 is disposed in camming engagement with the curved upper ends 57 of the fiber bundles 55 for resiliently urging the outer end surfaces 58 radially outwardly as the cam member 72 is moved axially downwardly, as illustrated in FIG. 4. It will be appreciated that the fiber bundles 55 are resiliently self-biased to their radially inwardly disposed position, illustrated in FIG. 3, so that they will naturally return to that position when the cam member 72 is retracted axially upwardly. For the purpose of adjusting the cam member 72, the set screws 79 are first loosened and the centering sleeve 60 is manually held stationary while the cam member 72 is adjusted, the set screws 79 being retightened after the adjustment has been made.

Figure 10:
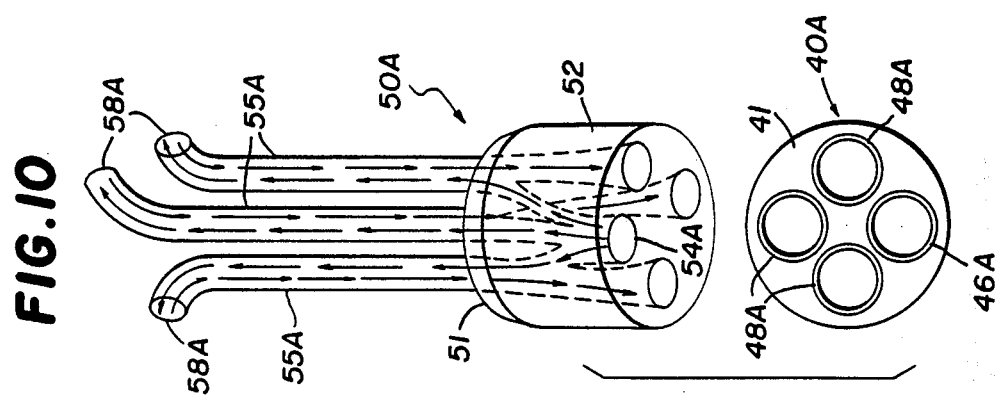
FIG. 10 is an enlarged, fragmentary, partially perspective and partially plan view, illustrating an alternative embodiment of the sensor assembly of the present invention.

In the embodiment of FIGS. 2–9, there is one emitter/detector unit 45 for each of the fiber bundles 55, so that each fiber bundle 55 has its own LED light source 46. Referring now to FIG. 10, there is illustrated an alternative embodiment of the present invention including a transducer assembly 40A and a sensor unit 50A. The transducer assembly 40A is similar to the transducer assembly 40, described above, except that there is mounted on the base 41 a single LED 46A and three phototransistors 48A. The sensor unit 50A is similar to the sensor unit 50, except that it includes three fiber bundles 55A. The upper ends of the fiber bundles 55A are curved and terminate in end surfaces 58A in the same manner as was described above with respect to the sensor unit 50. But at their lower ends, each of the fiber bundles 55A has a portion of its fibers separated and directed to a location 54A for alignment with the single LED 46A, while the remainders of the fiber bundles 55A are respectively disposed for alignment with the phototransistors 48A. Thus, there is provided a single high intensity light source which is common to all of the fiber bundles 55A and transmits light upwardly therethrough in the direction of the arrows in FIG. 10. Each fiber bundle 55A has its own phototransistor 48A, however, to which it transmits light downwardly in the direction of the arrows in FIG. 10.

In will be noted that the transducer assembly 40 and the sensor unit 50 are each of modular construction, so that they can be quickly and easily removed and reinstalled in the probe assembly 30, in the event of damage, contamination, malfunction or the like. This is in contrast to prior probe devices, wherein any damage or malfunction would necessitate replacement of the entire probe assembly.

Figure 11:
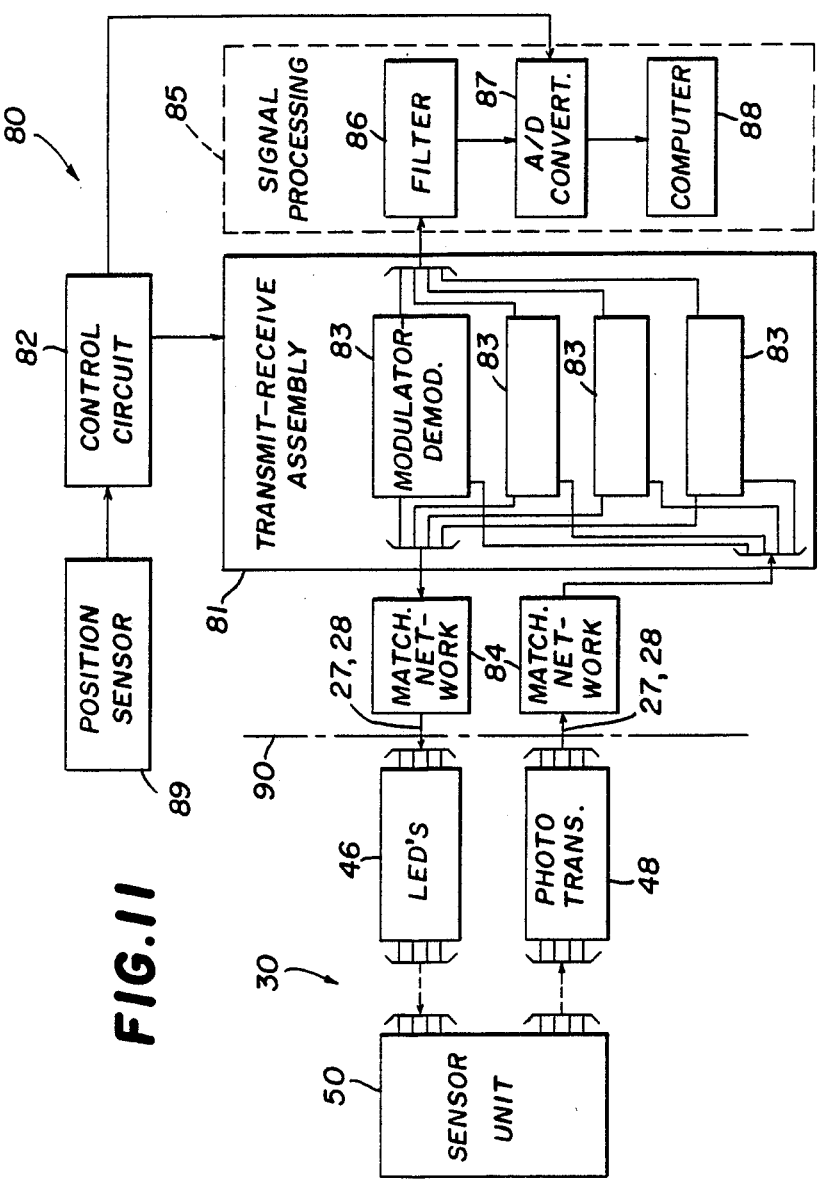
FIG. 11 is a block diagrammatic view of the control circuitry of the optical inspection system of the present invention.

Referring now also to FIG. 11, there is illustrated a control circuit 80 for controlling the operation of the probe assembly 30. In FIG. 11, the broken-line 90 indicates the boundaries of the steam generator vessel 10, it being appreciated that the probe assembly 30 is disposed within the steam generator vessel 10, and the control circuit 80 is disposed externally of the steam generator vessel 10, preferably at a remote location which may be as far as 500 feet from the steam generator vessel 10. The control assembly 80 includes a transmit/receive assembly 81 to which is coupled a control circuit 82. The transmit/receive assembly 81 includes a plurality of modulator/demodulators 83, equal in number to the number of phototransistors 48 utilized, i.e., either 3 or 4 in the preferred embodiments. Preferably, the modulator/demodulators 83 are commercially available circuits such as those sold by Banner Engineering Corporation. Each the modulator/demodulators 83 produces a modulated output which is applied through a matching network 84 to an associated one of the LED's 46. The modulation comprises a high-frequency (approximately 30 Khz) actuation and deactuation of each LED 46. In the embodiment of FIGS. 3–9, the LED's 46 of the three or four emitter/detector units 45 are respectively coupled to the modulated outputs of the modulator/demodulators 83. In the embodiment of FIG. 10, the single LED 46A is connected to the modulated output of one of the modulator/demodulators 83, the modulated outputs of the other modulator/demodulators 83 being unconnected.

As explained above, the LED's 46 or 46A are optically coupled to the fiber bundles 55 or 55A of the sensor units 50 or 50A. In the embodiment of FIGS. 3–9, each LED 46 is coupled to an associated one of the fiber bundles 55. In the embodiment of FIG. 10, the single LED 46A is optically coupled to a portion of the fibers of each of the fiber bundles 55A. The light from the LED's 46 or 46A illuminates the interior surface 17 of the tube 16 and is reflected therefrom, the reflected light being received through the fiber bundles 55 or 55A and applied to the phototransistors 48 or 48A. Each phototransistor 48 or 48A is responsive to the light signal received thereby for generating a corresponding light signal received thereby for generating a corresponding electrical signal which is applied through a matching network 84 to the input of an associated one of the modulator/demodulators 83.

Each of the modulator/demodulators 83 is designed to demodulate the modulated input signal. Thus, each modulator/demodulator 83 is resonsive only to a signal modulated at the predetermined modulation frequency, thereby rendering the circuitry substantially non-responsive to unmodulated ambient light. It will be appreciated that, in the case of multiple LED's 46, the LED's may all be modulated at the same frequency or, alternatively, each modulator/demodulator 83 may have a different modulation frequency, thereby greatly facilitating discrimination among the several receiving channels defined by the fiber bundles 55, and permitting ready discrimination among the different circumferential portions of the tube interior surface 17 viewed by the different fiber bundles 55.

Each of the modulator/demodulators 83 produces an analog output signal which is applied to a signal processing assembly 85. More specifically, the signal processing assembly 85 includes a filter 86 which receives the analog output signals from the modulator/demodulator 83, the output of the filter 86 being applied to an analog-to-digital converter 87 which produces a digital output applied to a computer 88, which may be a microcomputer. The analog-to-digital converter 87 is also coupled to the control circuit 82 for controlling the operation thereof. The control assembly 80 also includes a position sensor 89, which may be a rotary sensor, for determining the axial position of the probe assembly 30 within the tubes 16 relative to a predetermined reference position. The output of the position sensor 89 is also applied to the control circuit 82, so that the operator can, by the means of associated monitoring equipment (not shown), readily determine the position of the probe assembly 30.

It is a significant aspect of the invention that the control assembly 80 produces an unambiguous output signal which clearly distinguishes between the highly reflective honed surfaces and the dull or nonreflective unhoned surfaces of the tube 16. It will also be appreciated that, by the use of suitable software, the data from the position sensor 89 and from the sensor unit 50 or 50A can be combined to effectively generate a map of the interior surface 17 of the tubes 16. Because plural fiber bundles 55 or 55A and plural phototransistors 48 or 48A are utilized, it will be appreciated that substantially full circumferential coverage of the interior surface 17 of the tubes 16 can be achieved without having to rotate the probe assembly 30.

In a constructional model of the invention, the computer 88 may be a microcomputer, such as an IBM PC, XT or AT, and the remainder of the signal processing assembly 85 may be a data acquisition and control circuit, such as that sold by Metra Byte Corporation under the trademark DASH-16. The connector 31 may be a 20-contact connector of the type sold by LEMO USA Inc. under the designation FG3B320C0117.

From the foregoing, it can be seen that there has been provided an improved apparatus for inspecting the interior surfaces of tubes, the apparatus being of simple and economical construction, affording accurate and unambiguous indications of the tube condition, permitting simple sensitivity adjustments, and affording substantially complete circumferential coverage of the tube without rotation of the probe assembly.

I claim as my invention:

1. Apparatus for inspecting the interior surface of a tube, comprising: modulated infrared light source means, a plurality of light sensing means for receiving light from circumferentially spaced portions of the interior surface and generating electrical signals in response thereto, probe means for supporting said light source means and said light sensing means and moving them along the inside of the tube, and a tubular sleeve carried by said probe means and disposed for frictional sliding engagement with the interior surface of the tube for maintaining said probe means centered with respect to the tube as said probe means is moved along the tube, said sleeve surrounding at least a portion of said probe means, said sleeve including a plurality of resilient flexible fingers defining slots between said fingers for providing resiliency to said fingers, said fingers slidably engageable with the interior surface of the tube, and said sleeve having openings therein for accommodating the passage of modulated infrared light from said light source means to the interior surface and from the interior surface to said light sensing means.

2. The apparatus of claim 1, and further including position sensing means for determining the location of said probe means longitudinally of the tube.

3. The apparatus of claim 1, and further including means for modulating said light source means and for demodulating the electrical signals from said light sensing means.

4. The apparatus of claim 1, wherein said light source means includes a plurality of modulated infrared light emitting means equal in number to said light sensing means.

5. Apparatus for inspecting the interior surface of a tube, comprising: light source means, light sensing means for receiving light and generating an electrical signal in response thereto, fiber optic light transmitting means optically coupled to said light source means and to said light sensing means and defining an optical interface between said fiber optic light transmitting means and the interior surface of the tube, probe means for supporting said light source means and said light sensing means and said light transmitting means and moving them along the inside of the tube, and adjusting means carried by said probe means for selectively varying the distance between said optical interface and the interior surface of the tube.

6. The apparatus of claim 5, wherein said light transmitting means includes means for redirecting light.

7. The apparatus of claim 6, wherein said fiber optic light transmitting means defines said optical interface at one end thereof, said adjusting means effecting movement of said optical interface substantially radially of the tube.

8. The apparatus of claim 7, wherein said adjusting means includes means movable axially of the tube for adjusting said optical interface substantially radially of the tube.

9. The apparatus of claim 8, wherein said adjusting means includes cam means disposed for camming engagement with said fiber optic means.

10. The apparatus of claim 8, wherein said adjusting means includes threaded means for accommodating said axial movement.

11. The apparatus of claim 5, and further including a plurality of said light sensing means and a like plurality of said light transmitting means respectively defining a plurality of said optical interfaces, said adjusting means effecting simultaneous movement of said optical interfaces.

12. Apparatus for inspecting the interior surface of a tube, comprising: light source means, a plurality of light sensing means for receiving light and generating electrical signals in response thereto, fiber optic light transmitting means optically coupled to said light source means and to said light sensing means defining an optical interface between said fiber optic light transmitting means and the interior surface of the tube, probe means for supporting said light source means and said light sensing means and said light transmitting means and moving them along the inside of the tube, and adjusting means carried by said probe means for selectively varying the distance between said optical interface and the interior surface of the tube.

13. The apparatus of claim 12, and further including means for modulating said light source means and for demodulating the electrical signals from said light sensing means.

14. The apparatus of claim 12, wherein said light emitting means includes a light emitting diode and each of said light sensing means includes a phototransistor.

15. The apparatus of claim 12, wherein said light source means and said light sensing means and said light transmitting means are of modular construction for ready mounting in and removal from said probe means.

16. The apparatus of claim 12, and further including centering means carried by said probe means and disposed for frictional sliding engagement with the interior surface of the tube for maintaining said probe means centered with respect to the tube and for minimizing wobbling of said probe as said probe means is moved along the tube.

* * * * *